United States Patent [19]

Volk

[11] Patent Number: 5,440,458
[45] Date of Patent: Aug. 8, 1995

[54] ILLUMINATED LENS CASE

[76] Inventor: Donald A. Volk, 7893 Enterprise Dr., Mentor, Ohio 44060

[21] Appl. No.: 146,743

[22] Filed: Nov. 2, 1993

[51] Int. Cl.$^6$ .................. F21V 33/00; A45C 11/04
[52] U.S. Cl. .................................. 362/84; 362/154; 362/155; 362/253; 206/5.1; 108/26
[58] Field of Search ............... 362/382, 84, 155, 154, 362/253; 206/5.1, 6; 108/26, 25, 26.2; 220/632

[56] References Cited

U.S. PATENT DOCUMENTS

| | | | |
|---|---|---|---|
| 860,264 | 7/1907 | Stevens | 206/1 |
| 2,330,152 | 9/1943 | Spence | 206/6 |
| 2,517,248 | 8/1950 | Semeyn | 220/632 |
| 2,548,035 | 4/1951 | May | 220/632 |
| 2,780,348 | 2/1957 | Harter et al. | 206/1 |
| 2,935,209 | 5/1960 | Fritz | 108/25 |
| 3,532,213 | 10/1970 | Schulz | 206/62 |
| 3,572,560 | 3/1971 | Dolph | 224/5 V |
| 3,747,490 | 7/1973 | Brandt | 95/11 |
| 3,791,689 | 2/1974 | Boone et al. | 294/1 CA |
| 3,880,283 | 4/1975 | Flaherty et al. | 206/316 |
| 4,095,379 | 6/1978 | Weintraub | 312/209 X |
| 4,177,894 | 12/1979 | Petersen | 206/316 |
| 4,269,307 | 5/1981 | LaHaye | 206/5.1 |
| 4,431,041 | 2/1984 | Leiserson | 150/52 J |
| 4,442,478 | 4/1984 | Stansbury | 362/155 X |
| 4,545,479 | 10/1985 | Figari | 362/154 X |
| 4,574,944 | 3/1986 | Gregory | 206/5.1 |
| 4,609,975 | 9/1986 | Badolato et al. | 362/125 |
| 4,704,001 | 11/1987 | Parandes | 350/242 |
| 4,865,186 | 9/1989 | Gates | 206/5.1 X |
| 4,951,064 | 8/1990 | Kun et al. | 346/107 R |
| 5,042,655 | 8/1991 | Beldyk et al. | 206/316.1 |

Primary Examiner—Ira S. Lazarus
Assistant Examiner—Thomas M. Sember
Attorney, Agent, or Firm—Oldham, Oldham, & Wilson Co.

[57] ABSTRACT

An illuminated lens case for containing a plurality of diagnostic or therapeutic lenses used in eye examination and treatment in a darkened room comprises a container having a bottom wall, at least one side wall, and a top wall enclosing an interior space. One wall may be pivotally mounted to the container and adapted to swing between open and closed positions. The lens case further comprises a pair of vertically spaced horizontal shelf-like members which together with a side wall form a channel for attaching the lens case to a table top. A partition may divide the interior space of the container into a lens chamber and a battery and circuitry chamber. The lens chamber may contain an electroluminescent lamp in strip form at the bottom, and a lens holder having the plurality of recesses for receiving lenses disposed above the lamp. The lens holder is preferably made of polyethylene foam, which is both shock absorbing and translucent so as to diffuse light from the light source. The lens case may further include a battery and inverter with circuitry for powering the lamp, and a push button switch arranged so that the lamp is only illuminated when the top wall cover is open. Alternatively, a phosphorescent material may be disposed on the interior of the case to provide illumination.

17 Claims, 3 Drawing Sheets

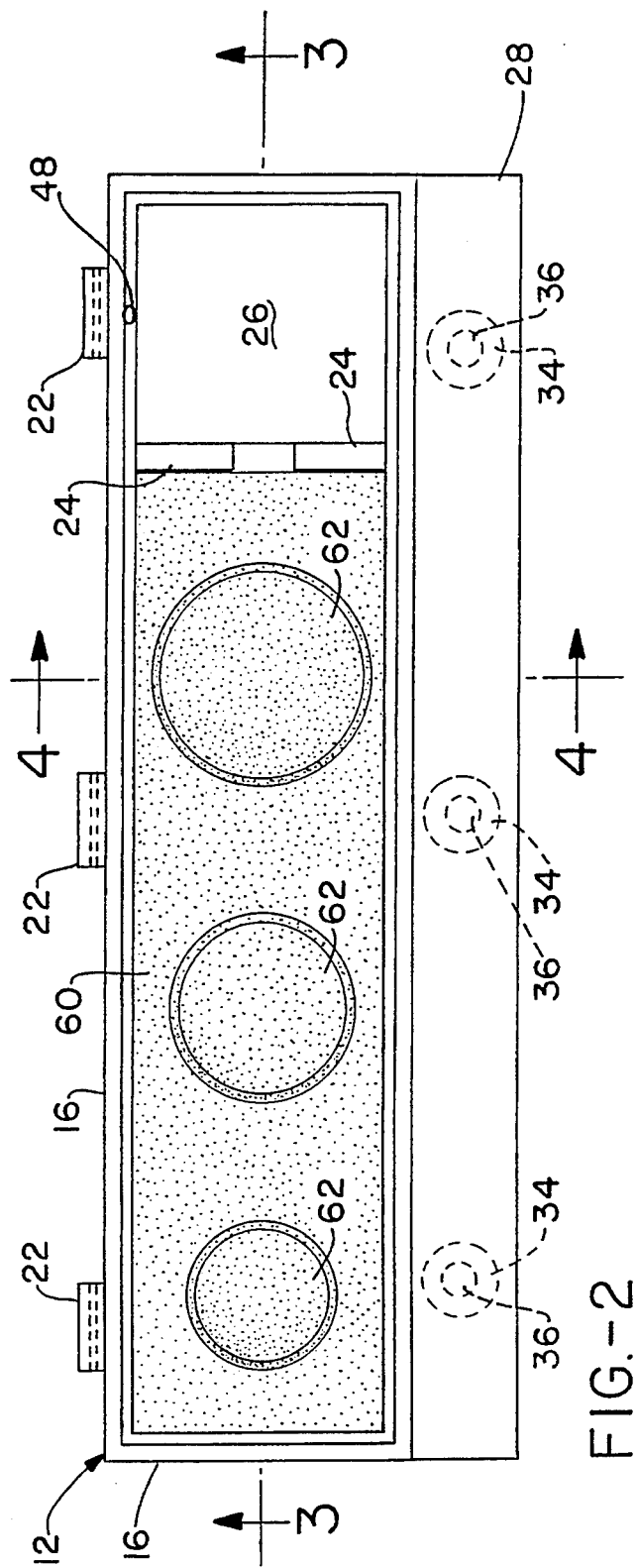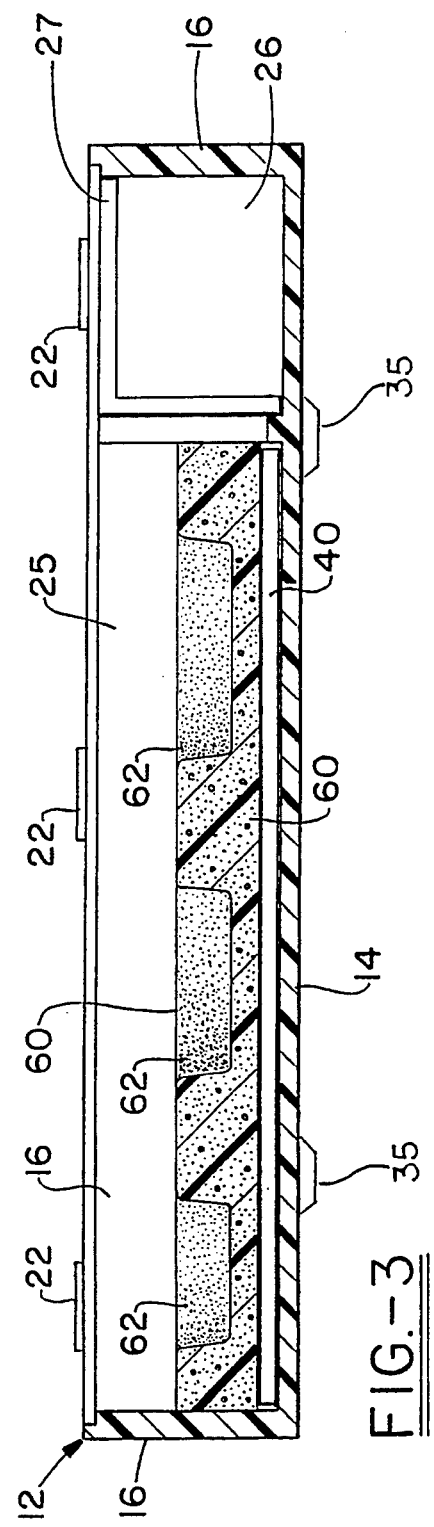

ILLUMINATED LENS CASE

TECHNICAL FIELD

This invention relates to illuminated lens cases and more particularly to an illuminated lens case for containing a plurality of lenses which are used in diagnostic procedures or treatment of a patient's eye in a darkened room.

BACKGROUND OF THE INVENTION

A variety of diagnostic and treatment procedures used in examination or treatment of the eye require a darkened room and the use of an ophthalmoscope, slit lamp biomicroscope, or operating microscope. These instruments will normally include a light source which is capable of directing light through the cornea and pupil of an eye being examined to the retina or other interior portion of the eye. These apparatus also include an imaging system used to visualize a portion of the eye, which is viewed by the observer. Direct or indirect ophthalmoscopy techniques are many times used in such procedures. For performing desired diagnostic or treatment procedures, the practitioner requires various optical lenses of different powers or functions, which should be readily available during examination. It is desirable to have these various lenses conveniently disposed within reach of the examiner.

Containers and carrying cases for various other types of lenses are known. These include, for example, contact lens cases and cases for carrying photographic lenses.

Also known are illuminated display cases in which objects such as trophies or merchandise for sale may be displayed. Such cases typically have a transparent front (and indeed the entire case except for typically the bottom wall may be transparent) and usually employ full-time illumination.

To the best of applicant's knowledge no one has addressed the needs of an ophthalmologist or optometrist in conducting diagnostic or treatment procedures in a darkened room. The examination or treatment of the eye requires a plurality of lenses which should be instantly at the examiner's disposal and identifiable in the darkened environment in which examination or treatment is conducted.

SUMMARY OF THE INVENTION

An object of this invention is to provide an illuminated lens case for a plurality of lenses which is particularly suitable for the needs of a practitioner performing diagnostic or treatment procedures of a patient's eye in a darkened room.

This invention provides an illuminated lens case comprising a container having a bottom wall, side walls and a top wall (or cover), one of which is hingedly mounted to the case and which together enclose an interior space in which a plurality of lenses may be stored. In a first embodiment, the case includes a light source, preferably an electroluminescent light source in strip form, a switch which causes the lens case to be illuminated upon opening of the top wall or cover, and a lens holder having a plurality of recesses shaped to receive particular lenses. In an alternate embodiment, the case includes phosphorescent material within the case which glows to allow the practitioner to identify and select a desired lens in the darkened room.

BRIEF DESCRIPTION OF THE DRAWINGS

The objects and advantages of the invention will become apparent upon further reading of the detailed description, in conjunction with the drawings, wherein;

FIG. 2 is a top plan view of the lens case shown in FIG. 1, with the cover removed.

FIG. 3 is an elevational view, in cross-section, as taken along line 3—3 of FIG. 2.

DESCRIPTION OF THE PREFERRED EMBODIMENTS

Figure 1:
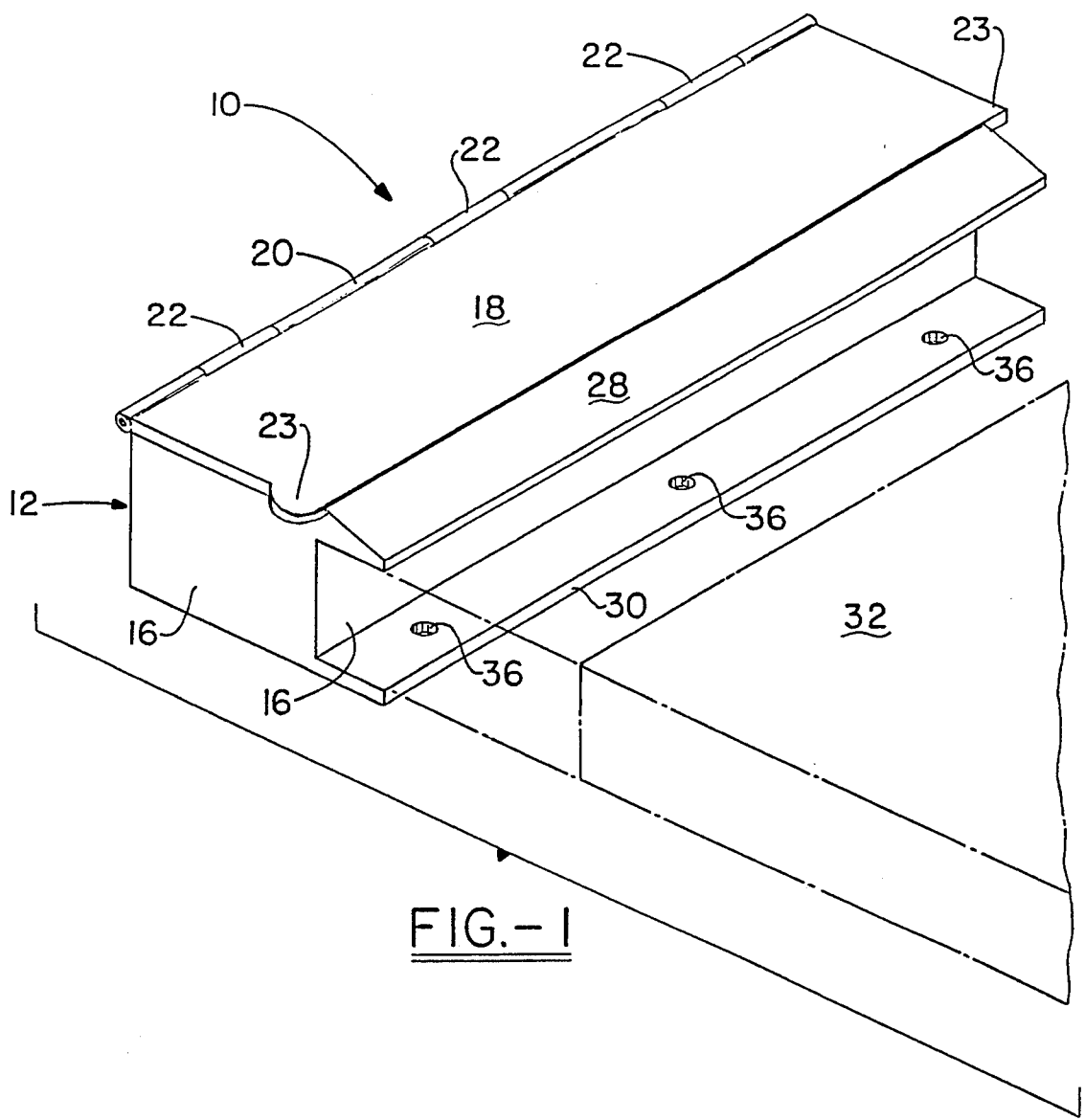
FIG. 1 is a perspective view of an illuminated lens case according to a preferred embodiment of the invention.

This invention will now be described in detail with respect to the accompanying drawings, which illustrate a preferred embodiment.

Referring now to FIGS. 1–4, 10 denotes generally a first preferred embodiment of an illuminated lens case in accordance with this invention. This lens case 10 of this invention is particularly suited for holding a plurality of optical lenses used by an ophthalmologist or optometrist in examination or treatment of the human eye. In particular, the lens case 10 of this invention may be used for containing a plurality of hand-held indirect ophthalmoscopy lenses. Examples of such lenses are disclosed in U.S. Pat. Nos. 4,682,866 and 4,738,521, both to David Volk. Typically, the lenses used by a practitioner in various diagnostic or treatment procedures have different functions and are of different sizes or configurations depending on the portion of the eye being examined, the magnification or imaging characteristics desired and other parameters.

The illuminated lens case 10 of this invention comprises a container 12, which includes a bottom wall 14, at least one upstanding side wall 16, and a top wall or cover 18. The preferred container 12 is of elongated, rectangular shape, with the bottom wall 14, the top wall 18, and four side walls 16, all being rectangular in shape. The four side walls 16 include two opposite longitudinally extending side walls and two opposite transversely extending side walls (which may be termed "end walls"). The bottom wall 14, the four side walls 16 and the top wall or cover 18 together enclose an interior space which is adapted to store a plurality of lenses. Each wall 14, 16, and 18 has an outside surface and an inside surface.

The illuminated lens case 10 is preferably formed of a rigid molded plastic, but may be formed of another material, such as wood or metal, which has sufficient strength and rigidity to contain a plurality of lenses and to withstand handling as lenses are placed in the lens case or removed therefrom. The lens case 10 is typically opaque.

The top wall or cover 18 is hingedly mounted along a top edge of container 12 (i.e., along the intersection of the top wall 18 with one of the two longer side walls 16). The top cover 18 is adapted to swing between open and closed positions by suitable hinge means. To this end, the cover 18 may have an annular hinge pin guideway 20 formed along one longitudinally extending edge thereof. The guideway 20 will receive a hinge pin (not shown) about which the cover 18 pivots when opening and closing. Hinge means may include a plurality of spaced conventional hinges 22 provided along the length of the top edge of the container 12 or any other suitable arrangement.

The cover 18 may swing through any desired arc upon opening thereof, usually at least 90° and preferably up to 270°, so that it will stay in the opened position for access to the interior of the container. The cover 18 may also be slightly longer than the bottom wall 14 over its width or portion thereof so as to provide an overhanging portion or tab 23 at one or both ends extending beyond the adjacent end wall 16 of the container. The tab 23 provides an aid in opening the cover. The drawings show an embodiment in which an overhanging portion or tab is provided at both ends, suitable for use in either of two mounting orientations.

A transverse partition 24, which may be bifurcated as shown, divides the interior space of container 12 into a lens chamber 25 and a battery chamber 26. The lens chamber 25 is adapted to receive a plurality of optical lenses for eye examination or treatment. The battery chamber 26 contains a battery to provide electrical power to an illumination system to be described hereinafter. The illumination system and a lens holder, also described hereinafter, are positioned within the lens chamber 25. Any other alternative arrangement for a battery power supply or other power supply can be used as desired. A battery cover 27 of generally L-shaped configuration is disposed above and on one side of the battery to enclose it within container 12.

The lens case 10 preferably has a pair of spaced and essentially horizontal, longitudinally extending shelf-like channel forming members 28 and 30 which extend from the exterior surface of a side wall 16, i.e., the elongated side wall on the side opposite hinges 22. The purpose of these channel forming members 28, 30 is to form with the adjacent side wall 16 a channel which will enable the lens case 10 to be clamped directly to a table 32 associated with the slit lamp biomicroscope or operating microscope, or any other table in an examination room. In the preferred embodiment, the upper channel forming member 28 is slightly tapered, decreasing in thickness from the upper edge of side wall 16 to the outer edge of the member 28. The tapered member 28 will form a smooth transition from case 10 to the table 32 on which it is secured. The selective positioning of the lens case 10 on the edge of a table 32 allows the lenses contained therein to be within easy reach of the practitioner without taking up table space. A plurality of reinforced sections 34, arranged in a row, may be provided on the underside of the lower channel forming member 30. The lower forming channel member 30 and the reinforced sections 34 have aligned holes 36 for receiving bolts or suitable means for clamping the lens case 10 to the table 32. For example, wing screws may be threadedly engaged in holes 36, to be tightened against the lower surface of the table 32 by hand to thereby hold the illuminated lens case 10 in place.

A low power light source 40 is provided in the interior space of container 12 to provide sufficient illumination to enable the ophthalmologist or optometrist to select a desired lens from case 10 in a darkened room. The illumination of the interior of case 10 must thus allow the practitioner to see and select the proper lens therefrom. In the preferred embodiment, the illumination light source is an electroluminescent lamp in strip form. This electroluminescent strip 40 is placed on the interior of container 12 at the bottom or inside surface of bottom wall 14, and extends the length of the lens chamber 25. Suitable electroluminescent lamps are known in the art. One such lamp is sold by Lamp Lighter Industries, Inc., of Yanceyville, N.C., under the trademark "PanELight TM". Another electroluminescent lamp is described in U.S. Pat. No. 4,951,064.

Figure 5:
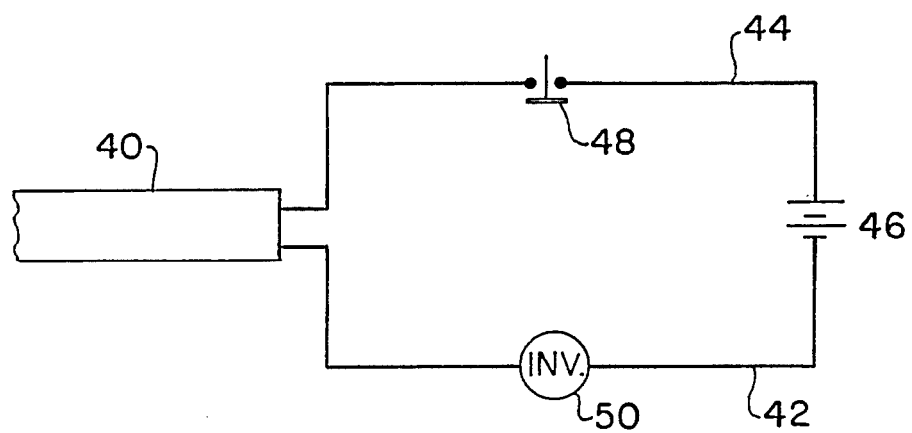
FIG. 5 is an electrical circuit diagram illustrating a preferred lighting system for the illuminated case of the present invention.
Figure 4:
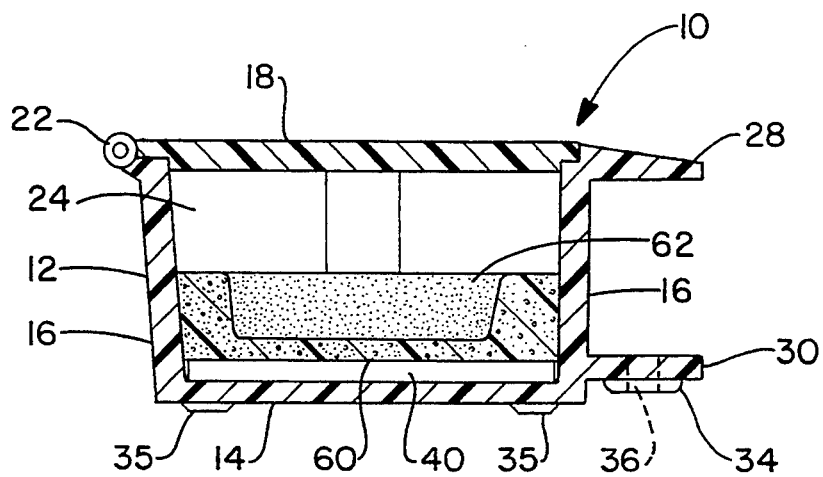
FIG. 4 is an enlarged elevational view, in cross-section, as may be taken along line 4—4 of FIG. 2 and with a cover in the closed position.

FIG. 5 shows an electrical circuit diagram showing the circuitry employed in the illuminated lens case 10 herein. Referring to FIG. 5, the illumination light source such as electroluminescent strip lamp 40 has electrical connections 42, 44 to a power source 46. The preferred power source is a 9-volt battery. The electrical circuit includes a push button switch 48 so that the electroluminescent lamp (or other light source) 40 will be illuminated only when the case 10 is opened. This push button switch 48 is situated adjacent to the top edge of one of the elongated side walls 16, either embedded in the sidewall or mounted on the inside surface of the sidewall adjacent to the top edge (see FIG. 2), so that the cover 18 when closed holds the push button switch 48 in the open position shown in FIG. 5. When the cover 18 is opened, the push button switch 48 (which is typically spring actuated) will move to the closed position, completing the circuit and causing strip 40 to be illuminated. In this way the interior space of the container 12 is illuminated when the cover 18 is open and is dark when the cover is closed to conserve battery power.

The preferred light source 40, i.e., an electroluminescent strip, operates on alternating current (AC). Since the battery 46 supplies direct current (DC), an inverter and associated circuitry 50, which converts direct current to alternating current, is provided. A voltage regulator or other means may also be used to supply proper voltage to the illumination source 40. Alternatively, the light source 40 may be connected via connections 42, 44 to an external power source, such as the power supply of a slit lamp biomicroscope or of the building rather than using the battery power supply. An electroluminescent strip is the preferred light source 40, because such a lamp has low power requirements and is available in thin strip form which occupies only a small amount of space along the bottom of the container 12. Alternatively, the electroluminescent lamp may be situated along one or both of the two longitudinally extending side walls 16, preferably near the top edge thereof. Alternatively, another type of light source, for example an incandescent or fluorescent lamp, which may be in tube form, may be used. An incandescent lamp will operate on either alternating current or direct current, so that an inverter may not be necessary.

A lens holder 60 for a plurality of diagnostic or treatment optical lenses is situated in the lens chamber 25 of container 12 above the electroluminescent strip 40. This holder 60 has a plurality of spaced apart recesses 62 for receiving lenses. Typically the lenses will be of different sizes and so the recesses 62 are of different sizes as shown. The holder 60 should be made of a shock absorbing material to afford maximum protection to the lenses. In addition, in the arrangement shown, the holder material is translucent, to allow light from the electroluminescent strip 40 to be diffused through the holder 60. This diffused lighting is superior because it gives low level, non-glare illumination within the lens case 10. A preferred holder material is polyolefin or polyethylene foam containing no color dyes, or in white color. The lens holder 60 is preferably removably disposed inside the interior space of lens chamber 25 so that it can be readily removed for access to the electroluminescent lamp 40 if necessary.

The illuminated lens case 10 of this invention is placed so that it is easily reached by the practitioner or other personnel. During an eye examination, when the practitioner requires a specific lens, he or she will open the cover 18 causing the lamp 40 to become illuminated to allow the proper lens to be easily located. When the professional has finished with that lens, it can be returned to its position in holder 60. Indicia may be provided on the lens holder 60 to facilitate identification and/or replacement of the selected lens.

A preferred lens case according to this invention will have a container 12 that is about 10" long, about 3" wide (inside dimensions) and about 1.5" high (inside dimensions). All walls are typically about 0.12" to about 0.15" thick. The overall width, including the channel forming members 28, 30 will be about 4.25". This will provide space typically for up to twelve lenses, depending on the lens diameters, with the lenses arranged in rows for example. These dimensions are representative and may be varied to suit individual needs. For example, the container 12 may be dimensioned to accommodate two rows of diagnostic lenses instead of a single row, or another configuration if desired.

The shape of container 12 is generally rectangular, since this is the shape that gives greatest ease of use and best space utilization. The container may be square cornered as shown, or the corners may be rounded or beveled. When beveled corners are used, the corners (which may be rounded) of cover 18 along the longitudinal edge which is away from the hinge mount 20 will provide tabs for ease of opening the cover 18, without any necessity of an overhang beyond the transversely extending side wall 16. A top opening lens case 10 as shown, in which the top wall or cover 18 swings open, is preferred. However, if desired, a front or side opening lens case may be provided. In that instance, one of the side walls 16 may be pivotally mounted along a top edge of the container, e.g., by a hinge arrangement similar to that shown. A plurality of lenses can then be positioned in vertically disposed recesses in lens holder 60.

The illuminated lens case 10 may also be arranged for resting on a flat table top or counter top surface if desired. For increased versatility, resilient feet 35 or other supporting members may be provided on the bottom corners of the container 12. Feet 35 may be formed of a material which will frictionally engage the table surface to inhibit sliding. Such an arrangement will permit either clamping to a table top or resting on a table top or counter top at the user's option. Alternatively, the channel forming members 28, 30 can be omitted altogether, with the case 10 simply designed for resting on a flat horizontal surface.

Figure 6:
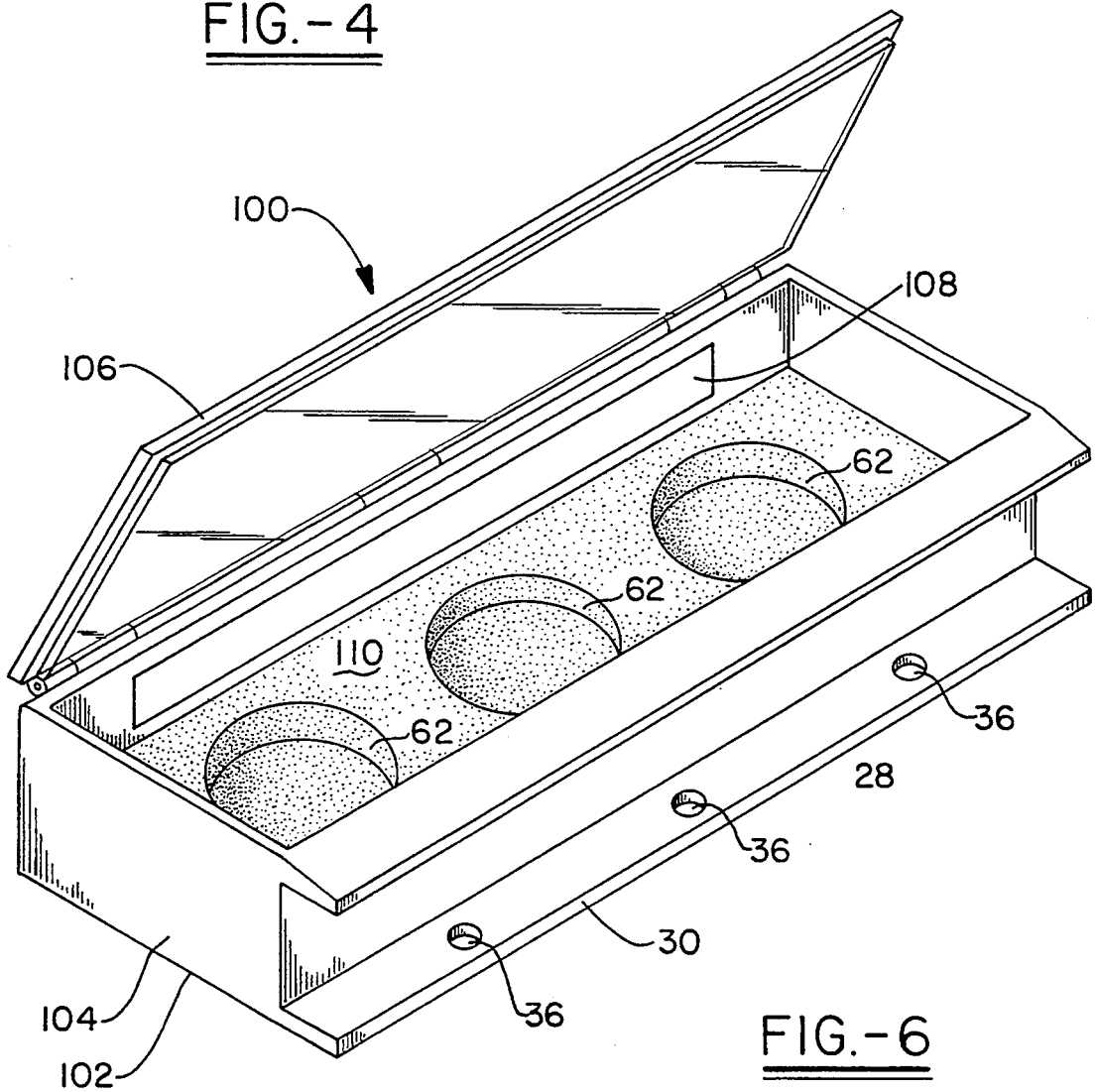
FIG. 6 is a perspective view of an alternate embodiment of the invention.

Turning now to FIG. 6, an alternate embodiment of the invention is shown, with the lens case generally designated 100. In this embodiment, similar aspects of the case 100 to that described in the previous embodiment have been designated by common reference numerals. Lens case 100 may again comprise a bottom wall 102, at least one upstanding side wall 104 and a top wall or cover 106 as in the previous embodiment. In this embodiment, lens case 100 includes a phosphorescent material 108, such as a phosphorescent paint or pressure-sensitive adhesive label material, which will glow upon darkening of the examination room. Alternatively, the entire case 100 may be formed of a plastic or other material which incorporates a phosphorescent material therein, such that the entire case 100 or portion thereof will produce a desired glow. The preferred lens case 100 will again include means to selectively clamp the case 100 to a table in the examination room. The phosphorescent material 108 will emit a sufficient glow to allow identification and selection of a desired lens from case 100. The phosphorescent material 108 is preferably located at an upper portion of case 100 to illuminate the plurality of lenses within a lens holder 110. In this embodiment, the lens holder may again be made of a shock absorbing material, but may be opaque, as light from the phosphorescent material 108 is not diffused therethrough and instead emanates from above lens holder 110. To facilitate identification of lenses within case 100, the lens holder 110 may again be white or a light color to better distinguish the lenses within holder 110. Additionally, as the phosphorescent material 108 will normally require exposure to light to provide a sufficient glow once the room is darkened. The cover 106 is therefore preferably made from a clear material to allow light transmission therethrough and onto the phosphorescent material 108. Phosphorescent material may also be provided on a corner of the cover 106 to facilitate opening and closing thereof in the darkened room. In this embodiment, no power is needed to generate a sufficient amount of illumination for identification and selection of desired lenses from the plurality of lenses stored within case 100.

While this invention has been described with particular reference to specific embodiments, including the best mode and preferred embodiment, it shall be understood that such description is by way of illustration and not limitation.

What is claimed is:

1. An illuminated lens case comprising:
    a container having a bottom wall, at least one side wall and a top wall which together enclose an interior space adapted to receive a plurality of individual and differing diagnostic or therapeutic optical lenses used for imaging or treatment of a patient's eye, each of said bottom wall, at least one side wall and top wall having an outside surface and an inside surface;
    at least one of said walls being hingedly mounted on said container and being adapted to swing between an open position and a closed position,
    a lens holder for said plurality of diagnostic or therapeutic optical lenses disposed in the interior space of said lens case and having a plurality of recesses for receipt of said optical lenses, and
    a source of light disposed in the interior space of said container for illuminating the area of said plurality of recesses for identification of said diagnostic or therapeutic optical lenses received therein.

2. An illuminated lens case according to claim 1, wherein said source of light is a lamp means connected to a power supply for supplying electrical power to said lamp means and including switch means for selectively causing said lamp means to be illuminated when said hingedly mounted wall is in an open position and not to be illuminated when said hingedly mounted wall is in closed position.

3. An illuminated lens case according to claim 2, wherein said lamp means is an electroluminescent lamp.

4. An illuminated lens case according to claim 2, wherein said power supply is positioned in said container.

5. An illuminated lens case according to claim 1, wherein,
said light source is a phosphorescent material provided on at least one of the interior surfaces of said walls in a manner to illuminate the area of said plurality of recesses in said lens holder.

6. An illuminated lens case according to claim 1, wherein said top wall is hingedly mounted along a top edge of said container and is adapted to swing between an open position and a closed position.

7. An illuminated lens case according to claim 1, further including a pair of vertically spaced and longitudinally extending horizontal channel forming members on the exterior of said container, said channel forming members and a side wall together forming a channel, said channel including attachment means associated therewith for enabling said container to be attached to a table along an edge thereof.

8. An illuminated lens case according to claim 1 wherein said lens holder is made of a translucent material and light from said source of light is diffused therethrough.

9. An illuminated lens case according to claim 8 wherein said translucent material is polyolefin or polyethylene foam.

10. An illuminated lens case according to claim 1 further including a transverse partition in said container for dividing said interior space into a lens chamber and a battery chamber, and a battery and associated circuitry in said battery chamber,
and wherein said light source is an electroluminescent lamp in strip form and disposed in said lens chamber,
and wherein further said lens holder is disposed in said lens chamber.

11. An illuminated lens case according to claim 10 wherein said lens holder is made of a translucent material and is disposed directly above said electroluminescent lamp.

12. An illuminated lens case according to claim 1 wherein said recesses in said lens holder are arranged at least one row.

13. An illuminated lens case according to claim 1,
wherein said interior space is divided by a partition into a lens chamber and a battery chamber,
wherein further said light source and said lens holder are disposed in said lens chamber, said light source being an electroluminescent lamp in strip form disposed along the inside surface of said bottom wall, said holder being translucent and disposed directly above said electroluminescent lamp;
said lens case further comprising a battery and inverter circuitry in said battery chamber, and a pair of vertically spaced and longitudinally extending horizontal channel forming members on the exterior of said container, said channel forming members and a side wall together forming a channel for enabling said lens illuminating case to be attached to a table along an edge thereof.

14. An illuminated lens case according to claim 1, wherein
said container includes a plurality of supporting members on the bottom surface thereof for supporting said container on a horizontal surface, said supporting members being formed of a material which will frictionally engage said surface to inhibit sliding of said container on said surface.

15. An illuminated lens case according to claim 1 further comprising,
a tab means associated with said hinged wall to facilitate opening and closing thereof.

16. An illuminated lens case according to claim 1, wherein
said source of light is a phosphorescent material disposed on at least one of the interior surfaces of said walls, and wherein at least one of said wall allows light to be transmitted therethrough to be incident upon said phosphorescent material.

17. An illuminated lens case according to claim 1, further comprising,
securing means on the exterior of said container for attaching said container to an article.

* * * * *